United States Patent
Fishman

(10) Patent No.: US 7,052,715 B2
(45) Date of Patent: May 30, 2006

(54) ALCOHOL-FREE TRANSDERMAL ANALGESIC COMPOSITION AND PROCESSES FOR MANUFACTURE AND USE THEREOF

(75) Inventor: Robert Fishman, Pembroke Pines, FL (US)

(73) Assignee: All Natural FMG, Inc., N. Palm Beach, FL (US)

( * ) Notice: Subject to any disclaimer, the term of this patent is extended or adjusted under 35 U.S.C. 154(b) by 580 days.

(21) Appl. No.: 10/412,626

(22) Filed: Apr. 11, 2003

(65) Prior Publication Data

US 2004/0202722 A1   Oct. 14, 2004

(51) Int. Cl.
*A61F 13/00* (2006.01)
*A61K 9/70* (2006.01)

(52) U.S. Cl. .................................... 424/449
(58) Field of Classification Search ................ 424/449
See application file for complete search history.

(56) References Cited

U.S. PATENT DOCUMENTS

| | | | |
|---|---|---|---|
| 5,885,597 A | 3/1999 | Botknecht et al. | |
| 6,346,278 B1 | 2/2002 | Macrides et al. | |
| 6,372,234 B1 | 4/2002 | Deckers et al. | |
| 6,416,772 B1 | 7/2002 | Van Engelen et al. | |
| 6,444,234 B1 | 9/2002 | Kirby et al. | |
| 6,528,040 B1 | 3/2003 | Pearson et al. | |
| 6,787,152 B1 * | 9/2004 | Kirby et al. | 424/449 |
| 2001/0006646 A1 | 7/2001 | Coyne | |
| 2001/0033838 A1 | 10/2001 | Farmer | |
| 2003/0031724 A1 | 2/2003 | Orthoefer et al. | |
| 2004/0202722 A1 * | 10/2004 | Fishman | 424/522 |
| 2004/0204343 A1 * | 10/2004 | Fishman | 514/3 |

* cited by examiner

*Primary Examiner*—Thurman K. Page
*Assistant Examiner*—Marc C. Fitzgerald
(74) *Attorney, Agent, or Firm*—McHale & Slavin, PA

(57) ABSTRACT

The instant invention is directed toward a dermal delivery system composition comprising an aqueous base vehicle including American Emu oil, Isopropyl Palmitate (PROTACHEM IPP), PEG-8 (a polyethylene glycol available under the tradename PROTACHEM 400), methylsulfonylmethane (MSM) and SEPIGEL 305 (a combination including polyacrylamide/$C_{13}$–$C_{14}$ Iso-paraffin and Laureth-7), in combination with an analgesic composition, such as ibuprofen, and to processes for the manufacture and use thereof.

6 Claims, No Drawings

ALCOHOL-FREE TRANSDERMAL ANALGESIC COMPOSITION AND PROCESSES FOR MANUFACTURE AND USE THEREOF

FIELD OF THE INVENTION

This invention relates to an analgesic composition in combination with an alcohol-free dermal delivery system for transdermal application and to processes for manufacture and use thereof.

BACKGROUND OF THE INVENTION

The treatment of illness often requires ingesting numerous pharmaceutical compositions. The treatment of pain particularly requires a level of active ingredients in a patient's bloodstream of sufficient concentration to maintain an analgesic or anti-inflammatory effect. To accomplish this, a patient must ingest a plurality of pills, capsules or the like, several times a day. This regimen is often difficult to maintain, given that the active ingredients, such as Acetylsalicylic acid and triethanolamine salicylate, or NSAIDs such as ibuprofen, naprosyn, and the like are associated with gastric irritation. While such irritation may only result in chronic stomach upset, in some cases this can quickly manifest itself in spontaneous gastric bleeding, which can be life threatening.

An additional problem associated with oral medications, is that the concentration levels which must be achieved in the bloodstream must be significant in order to effectively treat distal areas of pain or inflammation. These levels are often much higher than would be necessary if it were possible to more accurately target the particular site of pain or injury. Thus there exists a need for a transdermal analgesic formulation which is capable of distal application and which has the ability to alleviate pain and inflammation in a local fashion.

DESCRIPTION OF THE PRIOR ART

U.S. Pat. No. 6,416,772 teaches a topical dermal anesthetic composition for relief of pain comprising alcohol in an amount by weight of about 57 to about 91 percent; glycerin in an amount by weight of about 1 to about 12 percent; an analgesic agent in an amount by weight of about 2 to about 28 percent, the analgesic agent comprising a derivative of salicylic acid; methylsulfonylmethane in an amount by weight of about 0.02 to 5 percent; and emu oil in an amount by weight of about 0.01 to 3 percent. The composition provides transdermal pain when the analgesic agent is applied directly to an area of pain.

Alcohol, preferably ethyl or isopropyl alcohol, is taught as being necessary to effectively dissolve the analgesic so that it can be absorbed through the skin. Glycerin, in turn, is required to act as a stabilizer for the acetylsalicylic acid, triethanolamine salicylate, or other analgesic agent, such that the alcohol does not significantly affect the marketable shelf life of the composition. Glycerin is also taught as being necessary to sufficiently disperse the analgesic agent such that the composition does not need to be shaken or stirred before topical use. Methylsulfonylmethane and emu oil are taught as being included to help facilitate the absorption of the composition into the skin and also, due to the pain relieving characteristics in and of themselves, potentiate the analgesic to increase the efficacy of the composition.

This patent fails to teach a composition which is effective in alleviating pain when applied to various trigger points, distal from the actual perceived area of discomfort. Furthermore, the '772 patent requires the use of alcohol for transdermal delivery, which causes degradation of the analgesic, and subsequently requires glycerin as a stabilizer to retard the alcohol degradation.

U.S. Pat. No. 6,346,278 teaches a lipid extract of *Perna canaliculus* or *Mytilus edulis* as an active component, in a composition suitable for transdermal administration comprising an ointment or lotion base or vehicle, which may include a skin penetration enhancing agent to assist in administration of the active component. Suitable bases or vehicles are oils such as olive or emu oil, administered alone or with a penetrant such as cineole or limonene.

U.S. Pat. No. 6,444,234 teaches an alcohol containing pharmaceutical compositions for the transdermal administration of a medicament or other active agent by topical application of the composition to the skin of humans or other animals. Methodology for formulating such compositions which provide for very rapid uptake of the medicament and transmigration into and through the skin to either fatty tissues or the vascular system, while minimizing irritation to the skin and/or immunological response, is based on a transdermal delivery system (TDS) wherein the medicament is modified to form a true solution in a complex formed from particular solvents and solvent and solute modifiers in combination with skin stabilizers. Analgesics such as ibuprofen and the like, MSM and emu oil are taught as useful in combination with the transdermal delivery system.

U.S. Pat. No. 6,528,040 teaches an EMU oil-based formulation for use as an analgesic, anesthetic and antipruritic. The formulation contains 0.01 to 13 wt % alkyl esters; and 20 to 70 wt % Emu oil; 10 to 33 wt % benzyl alcohol; 10 to 33 wt % benzoin; 0.2 to 2 wt % allantoin; 0.25 to 1.25 wt % methylparaben and 0.01 to 0.30 wt % propylparaben. The formulation may be formulated as a spray or transdermal formula and may be used for treatment of chronic cutaneous ulcers and burn wounds.

U.S. Pat. No. 5,885,597 teaches a topical composition for relieving pain in a person in need of such relief, consisting essentially of an effective amount of a combination of at least one corticoid analgesic, at least one arylpropionic acid type analgesic, and at least one p-aminobenzoic acid ester type local anesthetic; an amount effective in enhancing the effectiveness in relieving pain of the combination of capsaicin, and an amount effective to increase the transmission thereof through the skin of at least one phospholipid and at least one polyoxyethylenepolyoxypropylene copolymer.

U.S. patent application Ser. No. 20030031724 teaches compositions that may be cost-effectively derived or processed from the emu, *Dromiceius novaehollandiae*, and used as anti-inflammatory agents in patients. The application does not contemplate the use of MSM or an analgesic agent in a transdermal delivery environment.

U.S. patent application Ser. No. 20010033838 teaches the use of emu oil and its various fractions as a carrier for antifungal, antibacterial, and antiviral medications and preparations. The use of MSM in combination with Emu oil is taught, however when transdermal application is desired the Emu oil is replaced with a liposomal or oil-based transdermal component.

SUMMARY OF THE INVENTION

Studies have shown that when NSAIDs and nutrients are taken orally, as little as 5% make it to the area of inflammation where they are needed. This is because of the stomach, liver and digestive system re-arranging and discarding much of them.

The instant invention discloses a dermal delivery system composition comprising an aqueous base vehicle including American Emu oil, Isopropyl Palmitate (PROTACHEM IPP), PEG-8 (a polyethylene glycol available under the trade name PROTACHEM 400), methylsulfonylmethane (MSM) and SEPIGEL 305 (a combination including about 40% polyacrylamide, about 15% $C_{13}$–$C_{14}$ Iso-paraffin, about 5% Laureth-7 and sterile water sufficient to make 100%).

To this base vehicle, an analgesic, illustrated by, albeit not limited to ibuprofen, is added.

In accordance with the instant invention, an analgesic composition is understood to include any pharmaceutical compositions having the ability to reduce or prevent pain, inflammation, or the like. Such compositions will include, but are not limited to mild analgesics such as aspirin and acetaminophen, NSAIDS (non-steroidal anti-inflammatory drugs) such as Indomethacin, Ibuprofen, Naproxen, Fenoprofen, Tolmetin Sulindac, Meclofenamate, Ketoprofen, Proxicam, Flurbiprofen, and Diclofenac, and various DMARDS (disease modifying anti-rheumatic drugs) such as corticosteroids, methotrexate and the like.

As opposed to the use of orally ingested analgesics, topical creams of the instant invention have several advantages. These advantages include:

1) Use of smaller amounts of active ingredients
2) Avoidance of liver metabolism
3) Avoidance of degradation of active ingredients in the gastrointestinal tract
4) Avoidance of irritation to the gastrointestinal tract The dermal delivery system, as illustrated herein, is alcohol free and therefore does not suffer from the problems of decreased shelf-life associated with alcohol containing prior art formulations. Since alcohol is not utilized, the presence of glycerin is likewise not required. Thus, a unique alcohol-free dermal delivery system is provided which provides enhanced penetration via the dermal layers thereby enabling a safer, quick-acting, and easier-to-comply alternative to capsules and tablets.

In various tests conducted between prior art formulations and those of the present invention, it has been discovered that the instantly disclosed formulations need not be placed directly on the source of perceived pain. Rather, the composition may be applied to various trigger points, distal from the point of pain perception, and pain relief will nevertheless be achieved.

Trigger Points are hyperirritable bundles of fibers within a muscle which become "knotted" and inelastic, unable to contract or relax, due to an injury. Trigger points have a number of causes such as overuse, injury, illness or even everyday stress. Trigger points in muscles shorten and tighten the muscle, stretching tendons and ligaments abnormally and reducing blood circulation in the muscle. When the muscle is tight, it lacks oxygen and the body releases chemicals that "trigger" pain. Thus, the instant inventors have found that application of the topical analgesic containing dermal delivery system to these trigger points results in a reduction or an elimination of pain in referred areas of the body.

Accordingly, it is an objective of the instant invention to provide an alcohol-free, cream base rapid dermal delivery system for transdermal dosing of an analgesic composition effective for the treatment of joint pain, stiffness, analgesic compositions.

It is a further objective of the instant invention to provide an analgesic composition for providing systemic relief from the discomfort of pain and/or inflammation when applied distal to the perceived source of discomfort.

It is yet another objective of the instant invention to provide a process for manufacture of a dermal delivery system.

It is a still further objective of the instant invention to provide a dermally applied formulation effective for reducing the production of prostaglandins.

Other objects and advantages of this invention will become apparent from the following description taken in conjunction with the accompanying drawings wherein are set forth, by way of illustration and example, certain embodiments of this invention.

DETAILED DESCRIPTION OF THE INVENTION

In order to reduce to practice a dermal delivery system which provides enhanced skin penetration it is necessary to understand the parameters which affect this phenomenon.

Various Factors Affecting Skin Penetration:

1) Oil solubility (J Pharm Sci "Linear relationships between lipophilic character and biological activity of drugs." 1972 January;61(1):1–19) the more oil soluble [lipophilic] the substance, the greater the skin penetration;

2) Molecular weight (the smaller the molecule, the easier penetrati

3) Creams, gels and liquids penetrate better than solids;

4) Penetration enhancers improve topical absorption of lipophilic substances (Targeted drug delivery to the skin and deeper tissues: role of physiology, solute structure and disease; Clin Exp Pharmacol Physiol 1997 November;24 (11):874–9).

EXAMPLE 1

In accordance with the instant invention, ingredients for a vehicle base are first selected.

| | |
|---|---|
| American Emu Oil | ~3% |
| Isopropyl Palmitate | ~3% |
| PEG-8 | ~4% |
| SEPIGEL 305 | ~3%* |
| (*additional in 1% increments, if needed for gelling) | |
| Methylsulfonylmethane | ~0.75% |
| Sterile (preferably Deionized) water to make up 100% | |

Formulation Procedure:

To the base vehicle as described above, active ingredient is added, for example ibuprofen. In this example up to about 10% active ingredient is contemplated.

1. Weigh out active ingredients, incorporate together in mortar and pestle. Mix until well blended;
2. Measure 3% American Emu oil into high speed mixing apparatus;
3. Add active ingredients to Emu oil. Mix until all powder is incorporated into oil. Mixture will be very dry;
4. Measure Isopropyl Palmitate and PEG-8, add to Emu mixture;
5. Let mix for ½ hour;
6. Add Sterile Water, mix for 5 minutes, scraping sides of mixing container occasionally; 7. Add SEPIGEL 305 3%, let incorporate for 5 minutes (If desired consistency has not been achieved, add SEPIGEL 305 1% increments until desired consistency is achieved).

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification.

One skilled in the art will readily appreciate that the present invention is well adapted to carry out the objects and obtain the ends and advantages mentioned, as well as those inherent therein. Any compounds, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. An alcohol-free analgesic composition effective for transdermal delivery consisting essentially of:
    about 3% Emu Oil, about 3% Isopropyl Palmitate, about 4% PEG-8, about 0.75% methylsulfonylmethane, and a gelling agent including a combination of about 40% polyacrylamide, about 15% $C_{13}$–$C_{14}$ Iso-paraffin, about 5% Laureth-7 and sterile water sufficient to make 100% in an amount effective for gelling, about 10% of an analgesic composition, and sterile water sufficient to make 100%.

2. A composition for treating the discomfort of pain and/or inflammation in a patient comprising:
    about 3% Emu Oil, about 3% Isopropyl Palmitate, about 4% PEG-8, about 0.75% methylsulfonylmethane, and a gelling agent including a combination of about 40% polyacrylamide, about 15% $C_{13}$–$C_{14}$ Iso-paraffin, about 5% Laureth-7 and sterile water sufficient to make 100% in an amount effective for gelling, about 10% of an analgesic composition, and sterile water sufficient to make 100%.

3. A process for treating the discomfort of pain and/or inflammation and pain in a patient comprising:
    identifying a location of pain and/or inflammation in a patient;
    identifying a location or trigger points associated with pain/or inflammation in a patient;
    transdermally delivering to at least one location of trigger point said points an analgesic composition consisting essentially of
    about 3% Emu oil, 3% Isopropyl Palmitate and about 4% PEG-8, about 0.75% methylsulfonylmethane, a gelling agent including a combination of about 40% polyacrylamide, about 15% $C_{13}$–$C_{14}$ Iso-paraffin, about 5% Laureth-7 and sterile water sufficient to make 100% in an amount effective for gelling, about 10% of an analgesic composition, and sterile water sufficient to make 100%;
    whereby the discomfort of said pain and/or inflammation is treated.

4. A process for manufacturing an alcohol-free analgesic composition effective for transdermal delivery comprising:
    providing said analgesic composition;
    providing about 3% Emu oil in a high speed mixing apparatus;
    adding said analgesic composition to said Emu oil and mixing until a homogeneously blended composition is formed;
    adding about 3% Isopropyl Palmitate and about 4% PEG-8 to said homogeneously blend, and mixing for approximately 30 minutes;
    adding sterile water and mixing for approximately 5 minutes, to homogeneity;
    adding about 3% of a gelling agent including a combination of about 40% polyacrylamide, about 15% $C_{13}$–$C_{14}$ Iso-paraffin, about 5% Laureth-7 and sterile water sufficient to make 100%, and blending to achieve homogeneity and a gel-like consistency; and
    adding additional said gelling agent in 1% increments, if necessary, until desired gel consistency is achieved.

5. The product produced by the process of claim 4.

6. An alcohol-free transdermal delivery system consisting essentially of:
    about 3% Emu oil, about 3% Isopropyl Palmitate, about 4% PEG-8, about 0.75% methylsulfonylmethane, a gelling agent including a combination of about 40% polyacrylamide, about 15% $C_{13}$–$C_{14}$ Iso-paraffin, about 5% Laureth-7 and sterile water sufficient to make 100% in an amount effective for gelling, and sterile water sufficient to make 100%.

* * * * *